(12) United States Patent
Brown

(10) Patent No.: US 10,016,616 B2
(45) Date of Patent: Jul. 10, 2018

(54) LASER DELIVERY APPARATUS WITH SAFETY FEEDBACK UTILIZING ENCODING OR MODULATION TO ENHANCE STIMULATED EMISSION OR REFLECTED FEEDBACK SIGNAL

(71) Applicant: Joe Denton Brown, Panama City Beach, FL (US)

(72) Inventor: Joe Denton Brown, Panama City Beach, FL (US)

( * ) Notice: Subject to any disclaimer, the term of this patent is extended or adjusted under 35 U.S.C. 154(b) by 123 days.

(21) Appl. No.: 14/739,192

(22) Filed: Jun. 15, 2015

(65) Prior Publication Data

US 2015/0360046 A1 Dec. 17, 2015

Related U.S. Application Data

(60) Provisional application No. 62/011,747, filed on Jun. 13, 2014.

(51) Int. Cl.
*A61N 5/06* (2006.01)
*A61N 5/067* (2006.01)

(52) U.S. Cl.
CPC .......... *A61N 5/06* (2013.01); *A61N 2005/063* (2013.01); *A61N 2005/067* (2013.01); *A61N 2005/0626* (2013.01)

(58) Field of Classification Search
None
See application file for complete search history.

(56) References Cited

U.S. PATENT DOCUMENTS

| 5,098,427 | A | 3/1992 | Hessel et al. | |
|---|---|---|---|---|
| 2007/0049911 | A1 | 3/2007 | Brown | |
| 2007/0167937 | A1 | 7/2007 | Brown | |
| 2008/0167671 | A1* | 7/2008 | Giordano | A61B 17/07207 606/167 |
| 2011/0238048 | A1* | 9/2011 | Brown | A61B 18/22 606/12 |
| 2011/0319877 | A1* | 12/2011 | Anderson | A61B 5/0059 606/10 |
| 2013/0129860 | A1 | 5/2013 | Chavez | |
| 2013/0218147 | A1 | 8/2013 | Brown | |

* cited by examiner

*Primary Examiner* — Ankit D Tejani
(74) *Attorney, Agent, or Firm* — Bacon & Thomas, PLLC

(57) ABSTRACT

A medical laser safety feedback apparatus and method enhances the detectability of a feedback signal from the treatment site by modulating or encoding an aiming or reference beam that is used to provide a stimulated emission or reflected component of the feedback signal.

8 Claims, 4 Drawing Sheets

LASER DELIVERY APPARATUS WITH SAFETY FEEDBACK UTILIZING ENCODING OR MODULATION TO ENHANCE STIMULATED EMISSION OR REFLECTED FEEDBACK SIGNAL

This application claims the benefit of Provisional U.S. Patent Appl. Ser. No. 62/011,747, filed Jun. 13, 2014, and incorporated herein by reference.

BACKGROUND OF THE INVENTION

1. Field of the Invention

This invention relates to an apparatus and method for delivering energy to a tissue, and in particular to an apparatus and method for enhancing the detectability of a feedback signal from the treatment site. The feedback signal may be the result of stimulated emission of phosphors provided in a target or instrument present at the treatment site, or by reflection of an aiming or reference beams from the target or instrument. According to the present invention, an independently-generated aiming or reference beam, or a beam derived from the primary therapeutic beam, is encoded or modulated in such a way as to enhance detection of the feedback signal and to distinguish it from general background radiation. The encoded or modulated feedback signal may be detected by any detector or spectrometer capable of discriminating between different wavelengths, amplitudes, timing, frequency spectra, and so forth.

2. Description of Related Art

Hazardous conditions that can occur during surgical procedures involving lasers include overheating or burning of tissues or equipment at the energy-delivery or treatment site. Numerous systems have been developed to detect such overheating or burning, including systems that directly detect the glow emitted by burning tissue, as disclosed in U.S. Pat. No. 5,098,427, systems that detect radiation by utilizing the introducer as a waveguide for radiation originating from the treatment site, as disclosed in the inventor's U.S. Patent Publication No. 2007/0167937, and systems that provide a radiation or temperature detector at the treatment site, such as the system disclosed in the inventor's U.S. Patent Publication No. 2007/0049911.

In PCT Publication No. 2013/012986 and U.S. Patent Publication No. 2013/0218147, the inventor proposed inclusion in the feedback signal of stimulated emission or reflected signals having a discrete signature to enhance the detectability of the feedback signals. The stimulated emission or reflected signals provide information about conditions at the treatment site based on attenuation of the signal resulting from build-up of contaminants at a distal end of said optical fiber, and are more easily distinguishable from background radiation due to the unique signatures of the signals, which are to be distinguished from pyrolytic or temperature based emissions indicative of burning or the temperature of said treatment area.

Despite the unique signatures, however, detection of stimulated or reflected radiation, and in particular distinguishing the stimulated or reflected radiation from radiation resulting from the treatment itself, including radiation emitted by the tissues as they are heated, is still difficult. The present invention solves this problem by adding an encoder or modulator to the safety feedback system.

An example of a system to which the principles of the invention may be applied is illustrated in FIG. 1. FIG. 1 shows a pulsed infrared medical laser system of the type used for breaking kidney stones. The system shown in FIG. 1 includes a laser apparatus A1 for generating and supplying laser energy to fiber 30. The apparatus A1 includes a laser head and power supply L1 for producing a therapeutic laser beam having a desired wavelength $\lambda 1$. A common laser apparatus for kidney stone applications is a Holmium laser that produces a wavelength of 2100 nm with up to 4 Joules of energy and a frequency as high as 50 Hz, although it will be appreciated that the invention may be applied to other types of laser systems, including lasers with a different output wavelength, energy, or frequency, and to applications other than kidney stone or other urological applications.

In the illustrated example, the primary Holmium laser beam $\lambda 1$ is partially split by a beam splitter S1. Output power is regulated by a control feedback circuit such that a small percentage of the primary laser beam $\lambda 1$ is directed and focused by lens assembly F1 into the photo-detector D1 and then analyzed by control circuit C1 in order regulate the power supply based on the feedback to ensure that the laser beam output has a predetermined wavelength, energy, and/or frequency. It will be appreciated by those skilled in the art that control circuit C1 may be an analog or microprocessor-based digital circuit, and that the present invention may be applied to systems with a variety of different types of laser power or output controller.

The remaining primary laser beam $\lambda 1$ of the system illustrated in FIG. 1 is focused by lens assembly F3 into optical fiber 30, which carries the beam to the treatment site. The operator fires the laser by depressing an external foot switch FS1. The laser apparatus A1 also generates a secondary laser beam $\lambda 2$ that is typically used as an aiming beam. The aiming beam $\lambda 2$ may, by way of example, be generated by a relatively low powered diode laser L2 having a 5 milliwatt output that generates a visible light beam of, typically, 630 or 532 nanometers. The output from the laser diode L2 is collimated by a second lens assembly F2 and directed onto the beam splitter S1, which combines the aiming beam $\lambda 2$ and primary beam $\lambda 1$ and directs the combined beam to the lens assembly F3 for coupling into the optical fiber 30.

SUMMARY OF THE INVENTION

In general, the invention modifies existing safety feedback apparatus and methods for controlling a medical or therapeutic laser by adding modulation or encoding of an aiming or reference beam, the aiming or reference beam stimulating phosphors at the treatment site or being reflected to provide a feedback signal.

The invention is applied to an apparatus for delivery of energy to a tissue within a patient, in which damage to the energy delivery device and/or harm to the patient is minimized by using optical feedback to detect conditions at the treatment site. The optical feedback signal is in the form of radiation emitted by a phosphor in response to stimulation by an aiming or reference beam, and/or by reflection of the aiming or reference beam. The aiming or reference beam may be a dedicated aiming beam or reference beam that is separate from the primary therapeutic beam, for example the output of an LED, or the reference beam may be a beam that has been separated from the primary therapeutic beam. In either case, the aiming or reference beam is encoded or modulated before coupling to the laser deliver fiber, in such as a way as to enhance the detectability of the feedback signal.

In the case of stimulated emission of phosphors, the phosphors may be applied to or included in a sheath into which the laser delivery fiber is inserted, a buffer material of the fiber, an endoscope working channel or other parts of the scope or laser delivery apparatus, and/or cardiac or urological stents. The phosphors can either be included in the material of the device or applied as a coating and/or treatment to the device or even tissues in the area of the targeted tissue. Suitable phosphors include rare earth phosphors, although other material that emits radiation having an identifiable signature at predetermined conditions may be used, including materials that convert IR wavelengths into visible or near visible wavelengths. Methods of detecting the radiation may include systems capable of discriminating between different wavelengths, amplitude, timing, frequency spectra, and so forth.

DETAILED DESCRIPTION OF THE PREFERRED EMBODIMENTS

Figure 1:
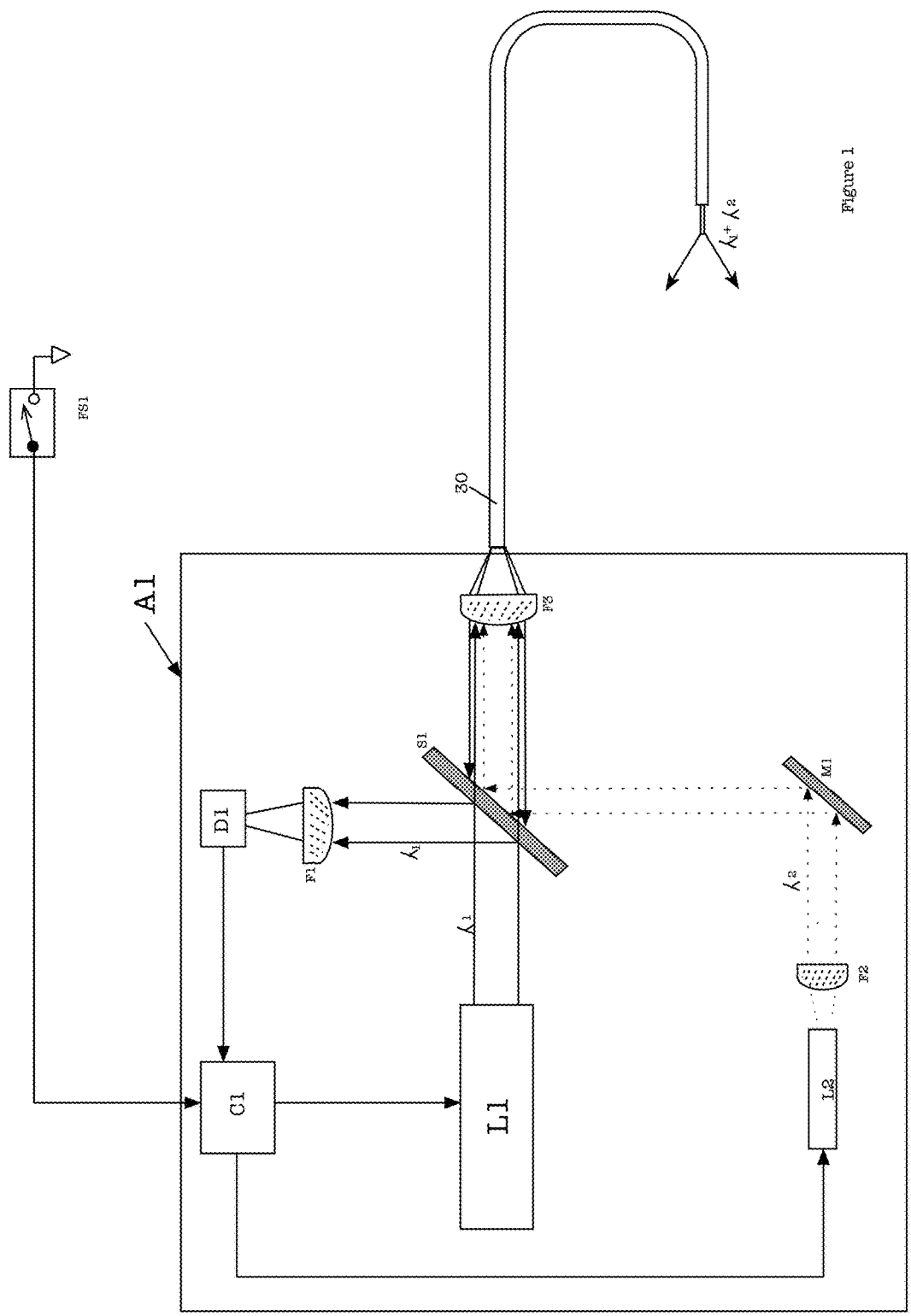
FIG. 1 is a schematic drawing of a conventional infrared pulsed medical laser system to which the present invention may be applied.
Figure 2:
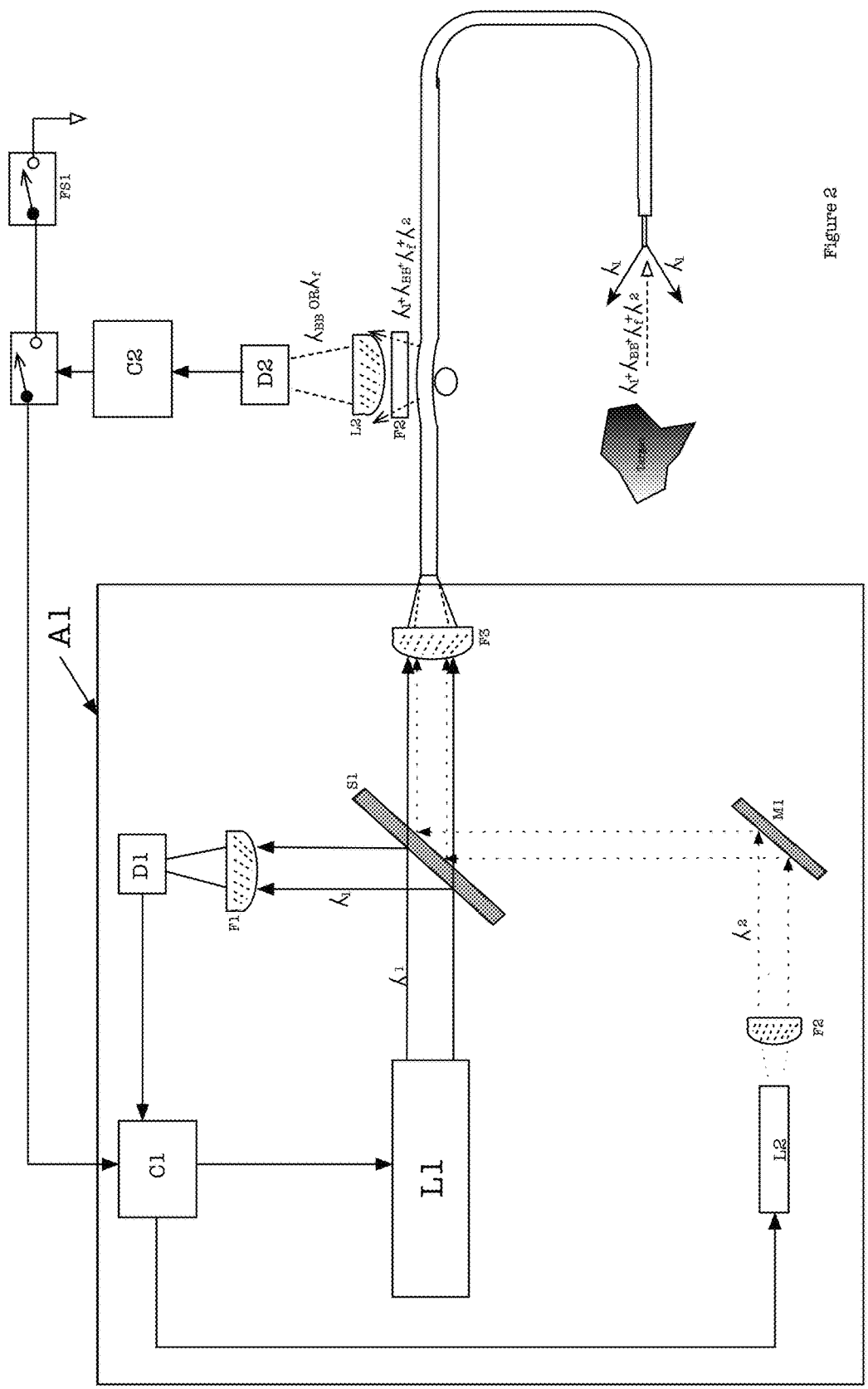
FIG. 2 is a schematic drawing showing a modified safety feedback system according to a first preferred embodiment of the present invention.
Figure 3:
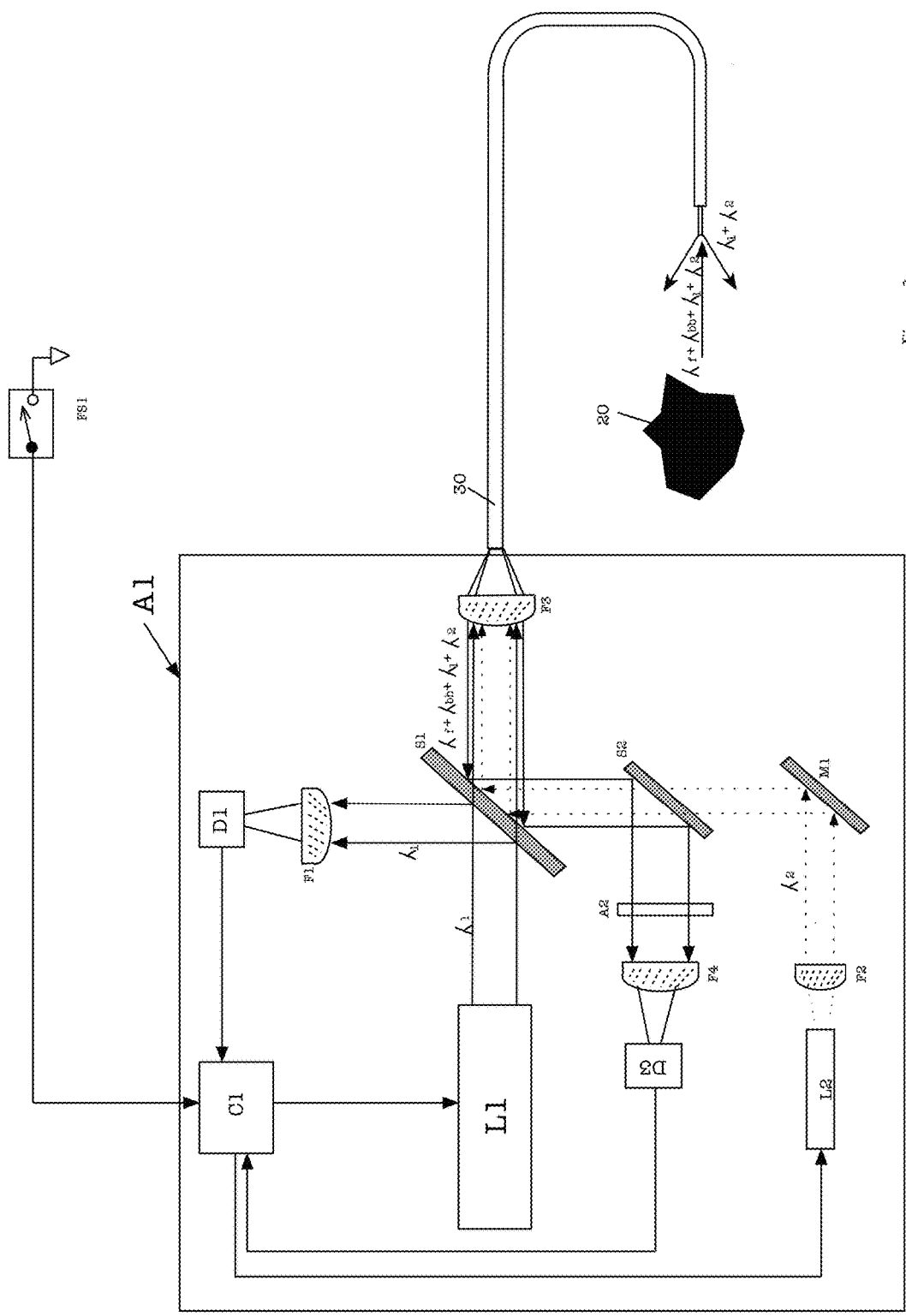
FIG. 3 is a schematic drawing showing a modified safety feedback system according to a second preferred embodiment of the present invention.

FIGS. 2 and 3 show preferred embodiments of the present invention, in which a second feedback detector is provided within the apparatus A1 of FIG. 1 (FIG. 3) or externally to the apparatus A1 (FIG. 2).

As with the system of FIG. 1, the preferred system of FIG. 2 includes a laser apparatus A1 for generating and supplying laser energy to fiber 30. The apparatus A1 includes a laser head and power supply L1 corresponding to those illustrated in FIG. 1 for producing a therapeutic laser beam having a desired wavelength $\lambda 1$. The laser apparatus may be a Holmium laser. However, it will be appreciated that the invention is not limited to a Holmium laser or to a particular output wavelength, energy, or frequency but rather may be applied to Nd:YAG lasers and other lasers used in medical procedures, and that the invention may be applied to applications other than kidney stone or other urological applications.

In the illustrated example, the primary laser beam $\lambda 1$ is again partially split by a beam splitter S1. Output power is regulated by a control feedback circuit such that a small percentage of the primary laser beam $\lambda 1$ is directed and focused by lens assembly L1 into the photo-detector D1 and then analyzed by control circuit C1 in order regulate the power supply based on the feedback to ensure that the laser beam output has a predetermined wavelength, energy, and/or frequency. The remaining primary laser beam $\lambda 1$ is focused by lens assembly F3 into optical fiber 30, which carries the beam to the treatment site. The operator fires the laser by depressing an external foot switch FS1.

It will be appreciated by those skilled in the art that control circuit C1 may be an analog or microprocessor-based digital circuit, and that the present invention is not limited to a particular type of laser power or output controller. The laser apparatus A1 also generates a secondary laser beam $\lambda 2$ that is typically used as an aiming beam. The aiming beam $\lambda 2$ may, by way of example, be generated by a relatively low powered diode laser L2 having a 5 milliwatt output that generates a visible light beam of, typically, 630 or 532 nanometers. The output from the laser diode L2 is collimated by a second lens assembly F2 and directed onto the beam splitter S1, which combines the aiming beam $\lambda 2$ and primary beam $\lambda 2$ and directs the combined beam to the lens assembly F3 for coupling into the optical fiber 30.

According to the present invention, a target that generates radiation having a wavelength $\lambda 3$ (or multiple wavelengths) in response to the aiming or reference beam is situated at the treatment site. The target may be part of the instrument, such as a sheath or the working channel of a scope, and may generate the reference beam by reflection or stimulated emission of a phosphorescent substance. The feedback signal may include not only reflected components of the aiming beam or reflected primary beam, but also blackbody radiation from the target $\lambda bb$ and fluorescence from the target $\lambda f$, and may be discriminated by wavelength, amplitude, timing, spectral analysis, or a combination of different detection methods.

Furthermore, alternate means for phosphor or reflected light to return from the target include using a small core fiber with side or reverse input in the working channel or look for the signal to leave the channel and pick it up with the camera of the endoscope. If the reflected signal (modulated or not) from the target was great enough to distinguish noise from data or scope versus a stone, then the phosphor may not be required FIGS. 2 and 3 show two exemplary ways of detecting and analyzing the feedback signal.

In the arrangement of FIG. 3, the laser apparatus A1 itself includes a feedback signal detection arrangement that may include, by way of example and not limitation, a filter A2, a focusing lens F2, and a feedback signal detector D3, which analyzes the feedback signal and provides the result to controller C1. A corresponding system is sold by Optical Integrity, Inc. under the name ScopeGuard™, but the present invention modifies the ScopeGuard™ system to modulate the aiming beam $\lambda 2$ output by laser L2 and to include a decoder or demodulator in the detector D3 or controller C1.

In the arrangement of FIG. 2, the filter A2, focusing lens F2, and feedback signal detector D3 are external to the laser apparatus A1. In this embodiment, the feedback signal is extracted from the optical fiber at a bend 10 in the fiber and supplied to a controller C2, which controls an interlock I1 and/or supplies the feedback signal to the main controller C1. A corresponding system is sold by Optical Integrity, Inc. under the name LaserGuard™, but the present invention modifies the LaserGuard™ system to modulate or encode the primary layer beam, or a portion thereof, and to include a decoder in either the detector D2 or external controller C2.

According to the present invention, either the aiming beam, the reference beam, or at least a portion of the therapeutic primary beam is encoded or modulated in such a way as to affect the detectability feedback beam $\lambda 3$, whether the feedback beam $\lambda 3$ results from stimulated emission from a phosphorescent material or reflection from a target or instrument at the treatment site.

The invention is not limited to a particular modulation or encoding technique. Techniques that may be suitable for different surgical or therapeutic applications include frequency modulation, amplitude modulation, frequency shift keying (FSK), phase shift keying (PSK), and pulse code modulation (PCM) techniques, or any other such techniques that enhance detectability of a signal irrespective of signal amplitude. In the case of modulation, it will be appreciated that the modulation range may be anywhere from zero to infinite Hertz. Where the primary beam is not visible, the modulation or encoding techniques must be applied to the aiming or reference beam (which may in turn be derived from the primary beam), whereas if the primary beam is visible, then the encoding or modulation techniques may be applied directly to a split part of the primary beam. Although a pulsed laser is illustrated, the encoding or modulation techniques of the invention may also be applied to continuous wave (CW) laser.

Figure 4:
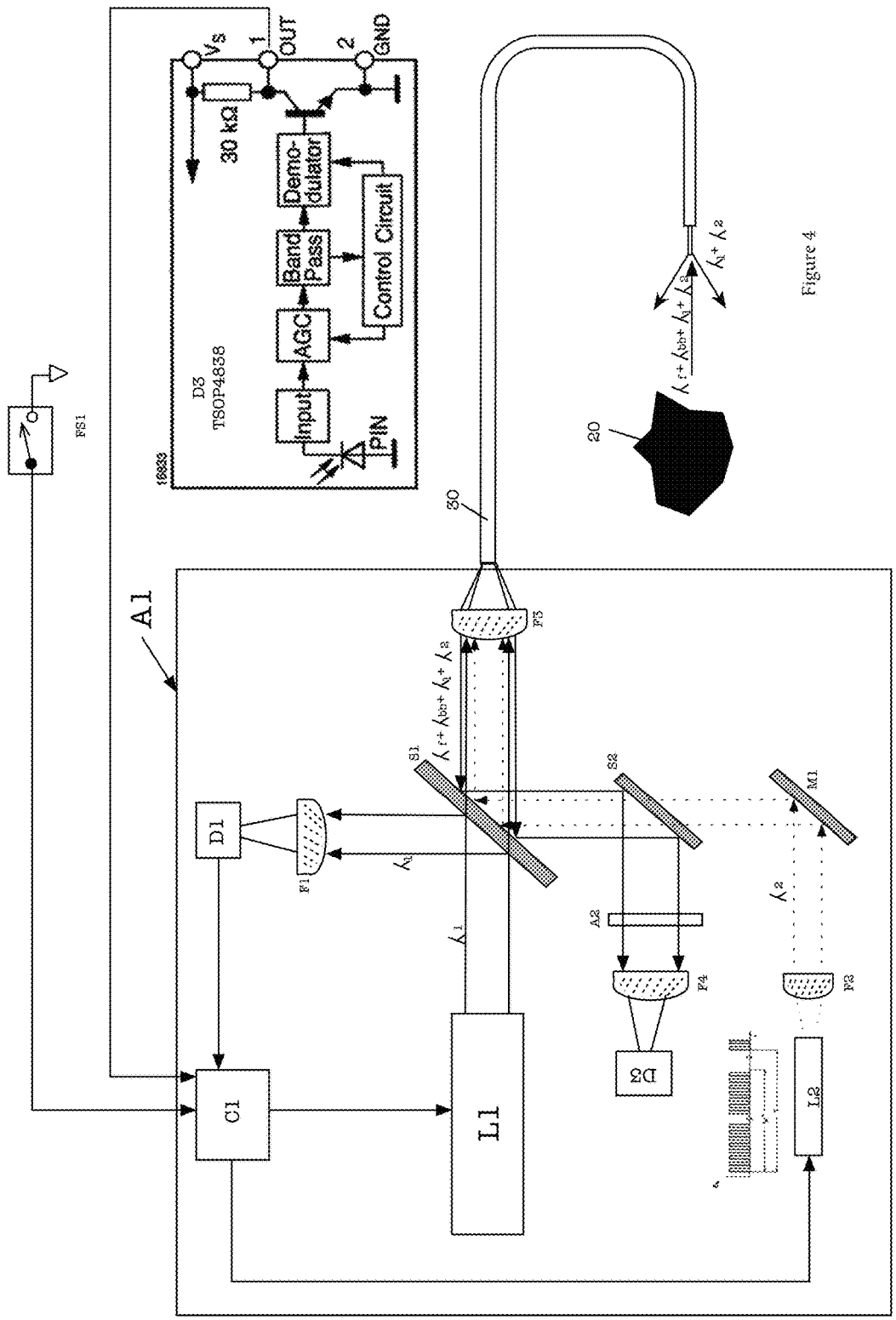
FIG. 4 is a schematic drawing showing a safety feedback system with a specific feedback signal demodulation circuit.

FIG. 4 shows, by way of example and not limitation, a specific implementation of the invention that utilizes a detector D3 arranged to demodulate a feedback signal arising from a modulated excitation laser. In the arrangement of FIG. 4, the laser controller, C1, modulates the excitation laser, L2, and thereby sets the modulation frequency for the reference beam, $\lambda_2$. By setting the frequency of the excitation beam, $\lambda_2$, to a predetermined value, detection of the phosphor emission, $\lambda_p$, is simplified since it will match the excitation beam's frequency. By looking for a specific frequency, the detector D3 can distinguish between wanted signals and all other sources of infrared noise. To further isolate the wanted signal, an optical filter, A2, can be used to filter out unwanted light spectra that may be present.

The block labeled BandPass in demodulator D3 represents an electronic filter that allows only the modulated frequency of choice to pass to the block labeled Control Circuit. Control Circuit controls the circuits labeled ACG (Automatic Gain Control) and Demodulator of detector D3. The gain control circuit ACG in detector D3 is used to vary the amplification of the input signal, $\lambda_p$, so that the signal corresponding to the phosphor's emission remains in the detection range of the detector D3 at all times. The circuit labeled Demodulator in detector D3 is used to turn the modulated signal, $\lambda_p$, into a digital signal which can be easily read and timed by the laser controller, C1.

In each of the illustrated embodiments and implementations, the demodulated or decoded feedback signal may be used for a variety of purposes, including determination of when power should be cut or a warning signal activated due to fiber break or fiber pull into the scope, or any number of undesirable potential failure suboptimal events In contrast to prior feedback systems where an event hit was required before making a shutdown decision, the feedback signal of the present invention may be used to modulate or shut down the therapeutic laser beam at any time before, during, and after a laser pulse. If a fast pulse has already started, a fast shutter may be activated to prevent the working channel from taking a hit.

Having thus described a preferred embodiment of the invention in sufficient detail to enable those skilled in the art to make and use the invention, it will nevertheless be appreciated that numerous variations and modifications of the illustrated embodiment may be made without departing from the spirit of the invention, and it is intended that the invention not be limited by the above description or accompanying drawings, but that it be defined solely in accordance with the appended claims.

What is claimed is:

1. A control unit for laser delivery apparatus including a laser system, an optical fiber for delivering energy from the laser system to a treatment area of a patient, said energy including a therapeutic laser beam and at least one of (a) an aiming beam, (b) a dedicated reference beam, and (c) a reference beam derived from the therapeutic laser beam, and for carrying a feedback signal from the treatment area back to the control unit, said feedback signal including at least one of (d) a phosphor emission stimulated by the aiming beam or the reference beams and (e) a reflection of the aiming beam or reference beams, said control unit including:

a modulation/encoding unit for modulating or encoding the aiming or reference beams to enhance detectability of the resulting phosphor emission or reflection of the aiming beam or reference beams; and a detection unit for detecting the phosphor emission or reflection of the aiming beam or reference beams.

2. A control unit as claimed in claim 1, wherein the detection includes a demodulation/decoding unit for demodulating or decoding the phosphor emission or reflection of the aiming beam or reference beams.

3. A control unit as claimed in claim 1, wherein the control unit analyzes the phosphor emission or reflection of the aiming beams by at least one of wavelength, amplitude, timing, frequency, and spectral analysis.

4. A control laser system for supplying energy to an optical fiber, the optical fiber delivering energy from the laser system to a treatment area of a patient, said energy including a therapeutic laser beam and at least one of (a) an aiming beam, (b) a dedicated reference beam, and (c) a reference beam derived from the therapeutic laser beam, and for carrying a feedback signal from the treatment area back to the control unit, said feedback signal including at least one of (d) a phosphor emission stimulated by the aiming beam or the reference beams and (e) a reflection of the aiming beam or reference beams, said laser system including a feedback control unit and the feedback control unit including:

a modulation/encoding unit for modulating or encoding the aiming or reference beams to enhance detectability of the resulting phosphor emission or reflection of the aiming beam or reference beams; and a detection unit for detecting the phosphor emission or reflection of the aiming beam or reference beams.

5. A control unit as claimed in claim 4, wherein the detection unit includes a demodulation/decoding unit for demodulating or decoding the phosphor emission or reflection of the aiming beam or reference beams.

6. A control unit as claimed in claim 4, wherein the control unit analyzes the phosphor emission or reflection of the aiming beams by at least one of wavelength, amplitude, timing, frequency, and spectral analysis.

7. A method of providing feedback for controlling a laser delivery apparatus including a laser system and an optical fiber for delivering energy from the laser system to a treatment area of a patient, said energy including a therapeutic laser beam and at least one of (a) an aiming beam, (b) a dedicated reference beam, and (c) a reference beam derived from the therapeutic laser beam, and for carrying a feedback signal from the treatment area back to the control unit, said feedback signal including at least one of (d) a phosphor emission stimulated by the aiming beam or the reference beams and (e) a reflection of the aiming beam or reference beams, said control method including the steps of:

modulating or encoding the aiming or reference beams to enhance detectability of the resulting phosphor emission or reflection of the aiming beam or reference beams; and detecting and analyzing the phosphor emission or reflection of the aiming beam or reference beams to determine when power should be cut or a warning signal activated due to fiber break or fiber pull into the scope or any number of undesirable potential failure suboptimal events.

8. A method of providing feedback for controlling a laser delivery apparatus as claimed in claim 7, further comprising the step of:
 demodulating or decoding a feedback signal that includes the phosphor emission or reflection of the aiming beam or reference beams.

\* \* \* \* \*